US012765832B2

(12) United States Patent
Imhauser

(10) Patent No.: US 12,765,832 B2
(45) **Date of Patent: *Oct. 20, 2026**

(54) APPARATUS AND METHOD FOR ASSESSING LAXITY OF A JOINT

(71) Applicant: New York Society for the Relief of the Ruptured and Crippled, maintaining the Hospital for Special Surgery, New York, NY (US)

(72) Inventor: Carl Imhauser, South Orange, NJ (US)

(73) Assignee: New York Society for the Relief of the Ruptured and Crippled, maintaining the Hospital for Special Surgery, New York, NY (US)

( * ) Notice: Subject to any disclaimer, the term of this patent is extended or adjusted under 35 U.S.C. 154(b) by 239 days.

This patent is subject to a terminal disclaimer.

(21) Appl. No.: 18/304,559

(22) Filed: Apr. 21, 2023

(65) Prior Publication Data

US 2023/0255551 A1 Aug. 17, 2023

Related U.S. Application Data

(63) Continuation of application No. 16/884,511, filed on May 27, 2020, now Pat. No. 11,660,044, which is a continuation of application No. 15/607,258, filed on May 26, 2017, now Pat. No. 10,667,746.

(60) Provisional application No. 62/341,791, filed on May 26, 2016.

(51) Int. Cl.
*A61B 5/00* (2006.01)

(52) U.S. Cl.
CPC .......... *A61B 5/4585* (2013.01); *A61B 5/6835* (2013.01)

(58) Field of Classification Search
CPC ............................ A61B 5/4585; A61B 5/6835
See application file for complete search history.

(56) References Cited

U.S. PATENT DOCUMENTS

| | | | | | |
|---|---|---|---|---|---|
| 4,633,867 | A * | 1/1987 | Kausek | A61F 5/0123 | 602/26 |
| 4,911,177 | A | 3/1990 | Lamb et al. | | |
| 5,335,674 | A * | 8/1994 | Siegler | A61B 5/103 | 600/595 |
| 9,521,965 | B2 | 12/2016 | Sena et al. | | |
| 9,566,022 | B2 | 2/2017 | Imhauser | | |
| 2013/0041289 | A1* | 2/2013 | Sena | A61B 5/4585 | 600/595 |
| 2017/0119284 | A1 | 5/2017 | Imhauser et al. | | |

* cited by examiner

*Primary Examiner* — Sameh R Boles
(74) *Attorney, Agent, or Firm* — Kim IP Law Group LLC

(57) ABSTRACT

An apparatus for evaluating motions of a joint is provided that is designed for determining stability of an anatomical joint. The apparatus includes a support frame, a fixation assembly for securing a first body segment of a joint, and a displacement assembly mounted to the support frame. The fixation assembly includes an axis of rotation moveable relative to the support frame. The displacement assembly includes a first frame pivotably mounted to the support frame and rotatably connected to a first end of the fixation assembly, and a second frame pivotably mounted to the support frame and rotatably connected to a second end of the fixation assembly.

18 Claims, 12 Drawing Sheets

APPARATUS AND METHOD FOR ASSESSING LAXITY OF A JOINT

CROSS-REFERENCE TO RELATED APPLICATIONS

This application is a continuation of U.S. patent application Ser. No. 16/884,511, filed May 27, 2020, which is a continuation of U.S. patent application Ser. No. 15/607,258, filed May 26, 2017, which claims the benefit of U.S. Provisional Application No. 62/341,791, filed May 26, 2016, the entire disclosures of which are incorporated by reference herein in their entirety for all purposes.

BACKGROUND OF THE INVENTION

The present invention relates generally to an apparatus and method for evaluating the stability of a joint. The apparatus relates to providing quantitative clinical measurements of an anatomical joint in a clinical or experimental environment.

Numerous instruments have been developed to provide quantitative clinical measurements of e.g., knee stability. Quantitative tests of e.g., anterior-posterior stability rely on application of a force at the center of the knee joint, and measurement of translation with respect to a point at the center of the knee. However, clinicians are often interested in the individual anterior-posterior stability of the medial and lateral compartments of the knee to differentiate the effects of injury (e.g., ACL rupture) and treatment (e.g., ligament reconstruction and joint replacement).

Knee rotations and coupled motions as measured during clinical examination of the knee (pivot shift mechanism) are an important predictor of clinical outcome and a potential risk factor for osteoarthritis following ligament injuries, such as ACL ruptures. Quantitative tests of rotational stability rely on applying pure torques about a fixed axis. However, the axis of rotation of the knee changes with flexion angle, and is affected by knee injury, ligament reconstructions, or joint replacement. Therefore, identifying the location of the axis of rotation would provide additional novel information to discriminate knee function beyond conventional devices that rely on a measurement of knee rotations about a fixed and predetermined axis of knee rotation. Conventional measurement devices are unable to provide such data.

Thus, there is still a need in the art for an apparatus for evaluating motions of a joint and laxity thereof that can effectively identify the location of an axis of rotation and allow for application of forces on the joint to independently measure stability of the joint.

BRIEF SUMMARY

In accordance with an exemplary embodiment, the subject disclosure provides an apparatus for evaluating motions of a joint comprising a support frame, a fixation assembly for securing a first body segment of a joint, and a displacement assembly mounted to the support frame. The fixation assembly includes an axis of rotation moveable relative to the support frame. The displacement assembly includes a first a first frame pivotably mounted to the support frame and rotatably connected to a first end of the fixation assembly, and a second frame pivotably mounted to the support frame and rotatably connected to a second end of the fixation assembly.

In accordance with another exemplary embodiment, the subject disclosure provides an apparatus for evaluating motions of a joint comprising a support frame, a fixation assembly for securing a first body segment of a joint and connected to the support frame, and a displacement assembly mounted to the support frame. The fixation assembly includes a floating axis of rotation relative to the support frame. The displacement assembly includes a first frame mounted to the support frame and rotationally connected to a first end of the fixation assembly, and a second frame mounted to the support frame and rotationally connected to a second end of the fixation assembly.

The exemplary embodiments of the subject disclosure provide an apparatus developed, for example and not by way of limitation, to measure individual anterior-posterior translations of the medial and lateral compartments of a knee, and to identify both an angle of rotation and a location of an axis about which the knee rotates. The apparatus can also apply pure torques about a long axis of a bone, e.g., the tibia. The exemplary apparatus can also apply equal anterior-posterior forces or displacements to the medial and lateral sides of the knee.

The exemplary embodiments of the subject disclosure also provide a force couple mechanism. The force couple mechanism allows simultaneous or independent application of anterior-posterior forces e.g., to the medial and lateral sides of the knee. In an exemplary example, the femur of the patient is stationary, while the tibia is fixed to the force couple mechanism using a brace. The anterior-posterior forces are applied to the tibia through the brace either manually or via actuators located on the medial and lateral sides of the tibia. The force applicators are in parallel with positional sensors and in series with force sensors to quantify the load-displacement response of the medial and lateral compartments of the knee. Measurement of the displacement of each of the actuators combined with the fixed distance between the actuators allows the angle of rotation and the location of the axis of rotation to be determined.

One exemplary embodiment of the subject disclosure focuses on application of anterior-posterior forces to the tibia with the femur fixed in place or stationary. However, the principles of the exemplary embodiment can also be adapted to testing the knee joint about another anatomical axis. For example, a force couple mechanism can be applied about an anterior-posterior axis of the knee, which provokes varus and valgus rotation of the knee.

It is to be understood that the exemplary embodiments of the subject disclosure can also be adapted to other joints, e.g., cervical spine, ankle joint complex, shoulder joint, hip joint, etc.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the subject disclosure, there are shown in the drawings exemplary embodiments. It should be understood, however, that the exemplary embodiments of the subject disclosure are not limited to the precise arrangements and instrumentalities shown.

In the drawings.

DETAILED DESCRIPTION OF THE INVENTION

Figure 1:
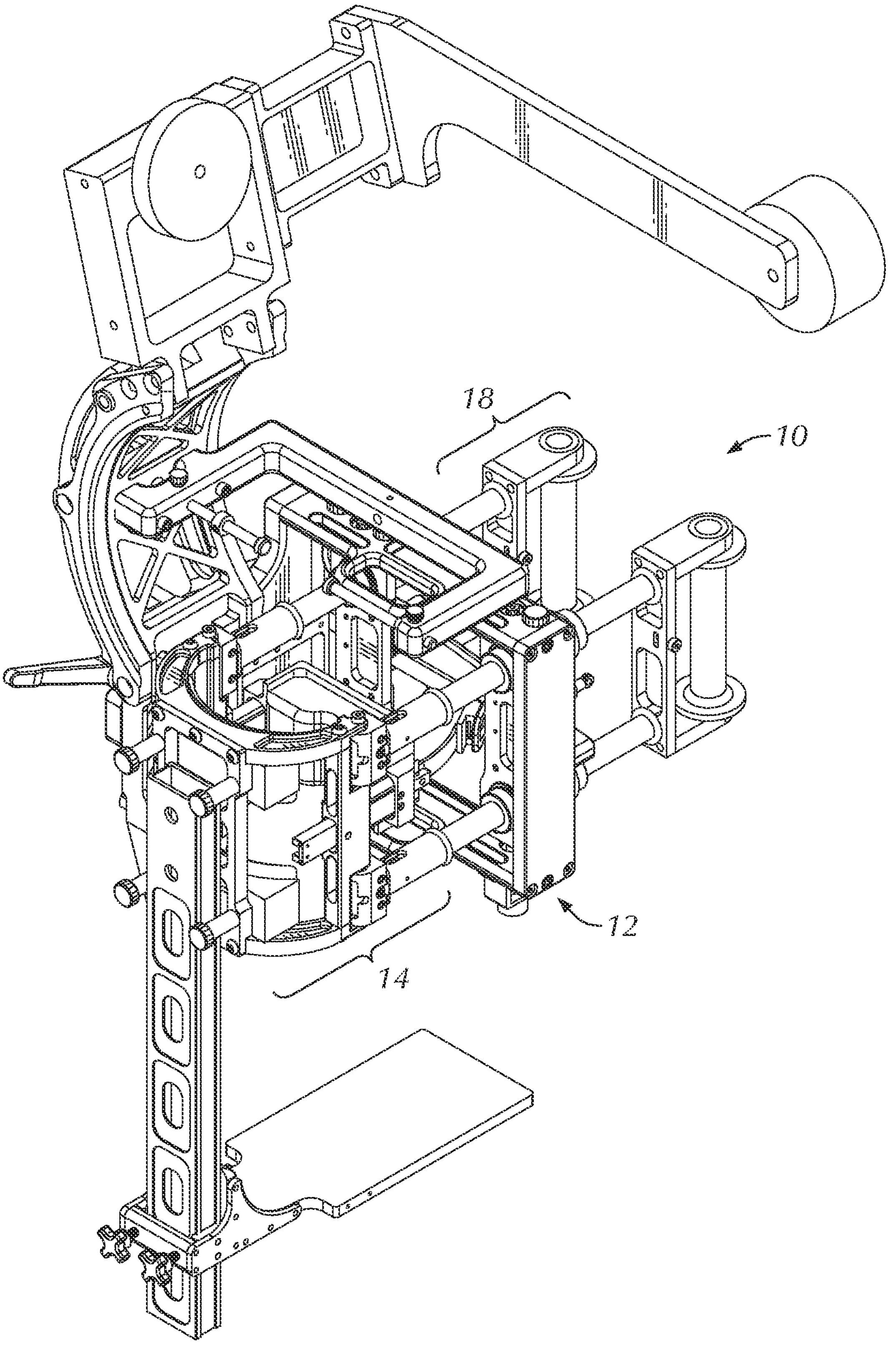
FIG. 1 is a perspective view of an apparatus for evaluating motions of a joint in accordance with an exemplary embodiment of the subject disclosure.
Figure 2:
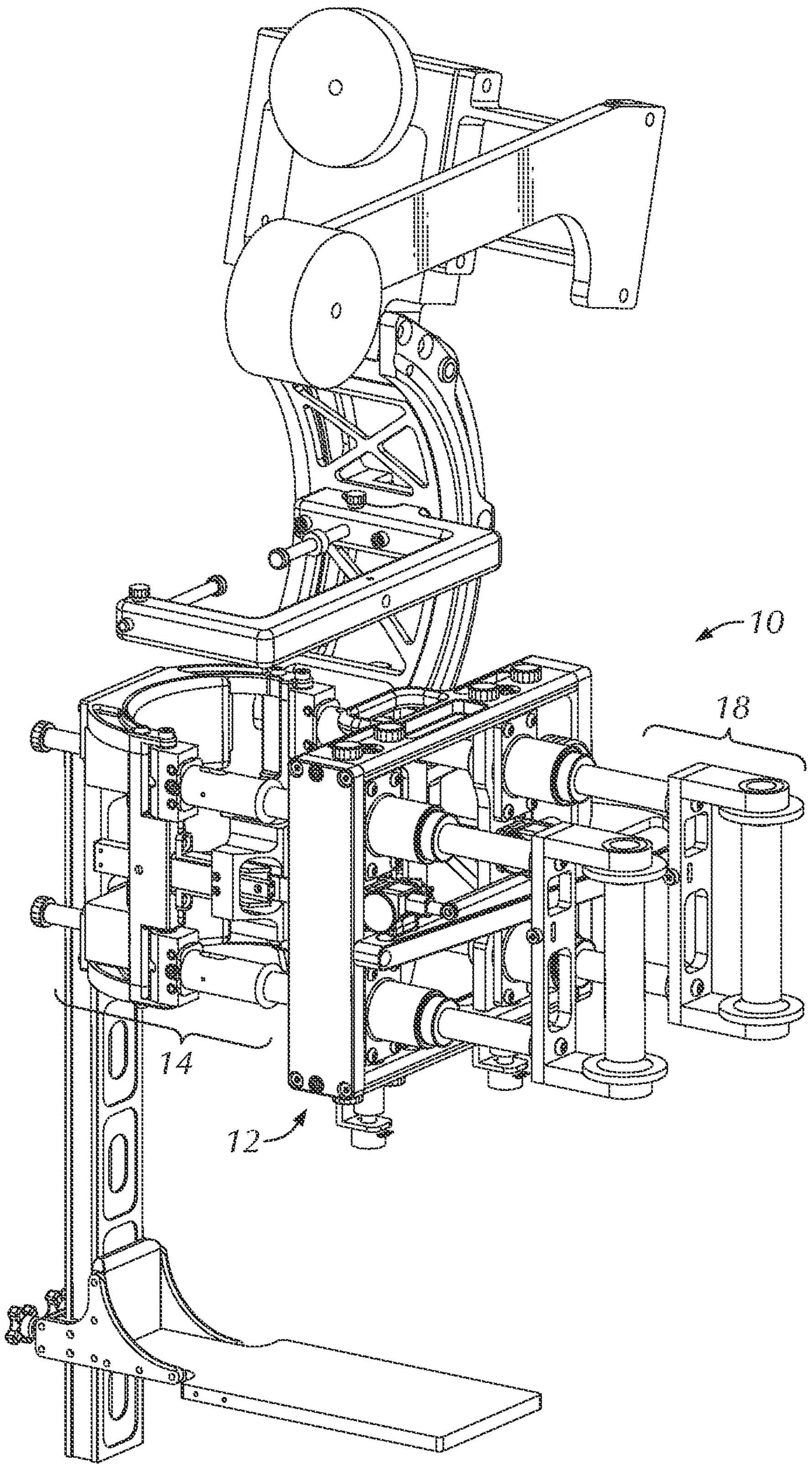
FIG. 2 is another perspective view of the apparatus of FIG. 1.
Figure 3:
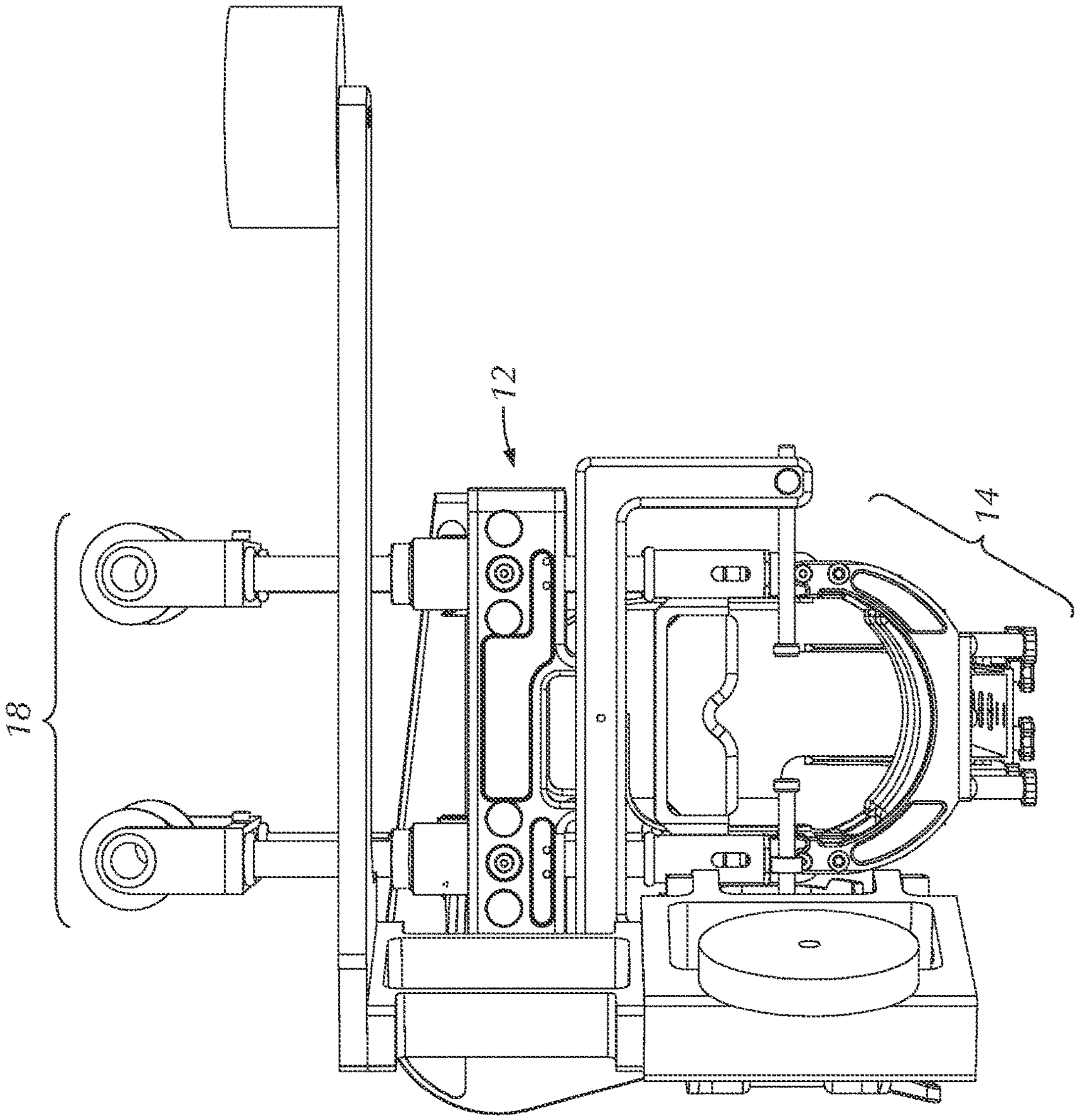
FIG. 3 is a top perspective view of the apparatus of FIG. 1.
Figure 4:
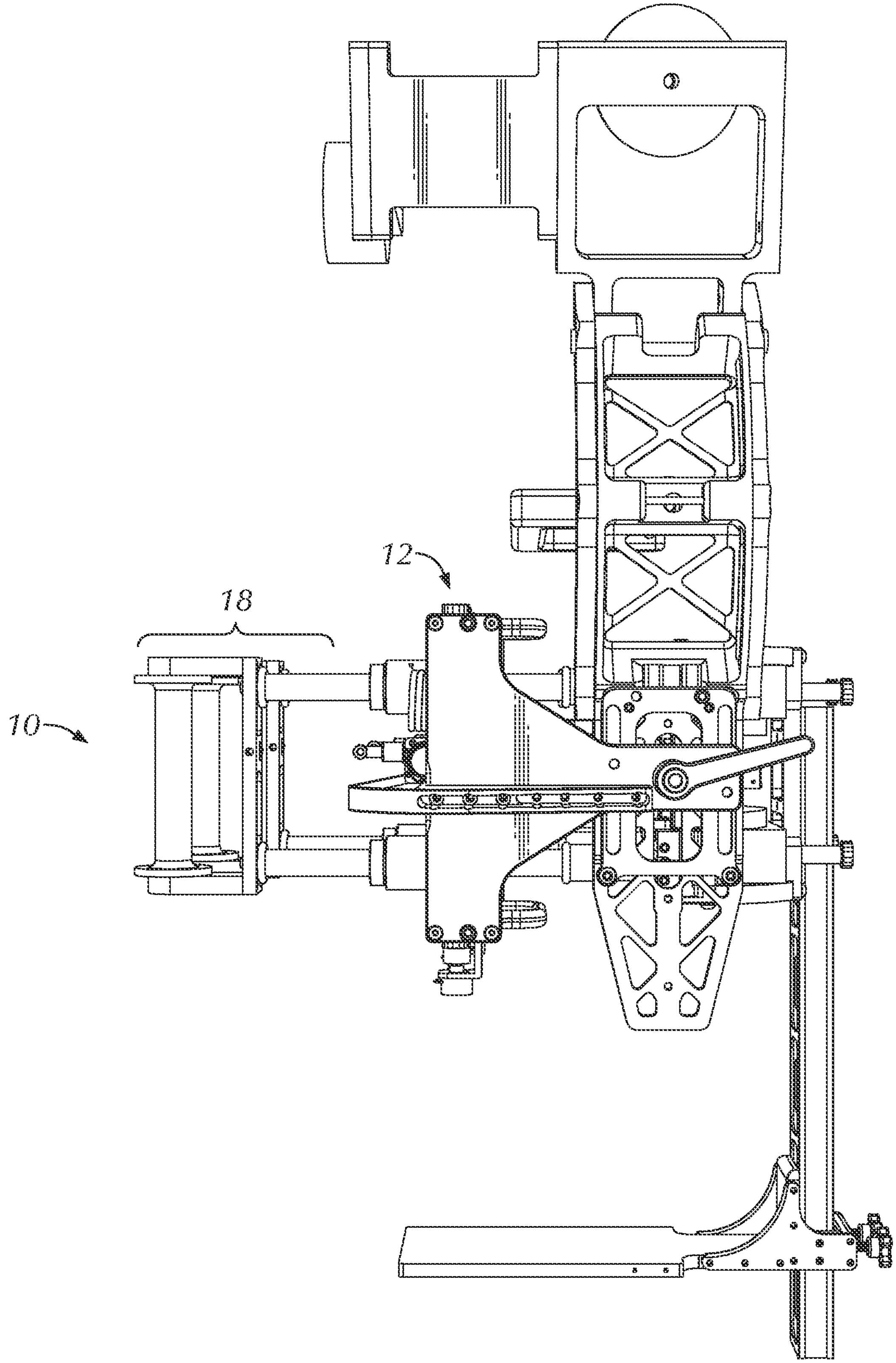
FIG. 4 is a side perspective view of the apparatus of FIG. 1.

Reference will now be made in detail to the exemplary embodiments of the disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. Such directional terms used in conjunction with the following description of the drawings should not be construed to limit the scope of the exemplary embodiments in any manner not explicitly set forth.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the identified element and designated parts thereof. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

Throughout this disclosure, various aspects of the exemplary embodiments can be presented in a range format. It should be understood that the description in range format is merely for convenience and brevity and should not be construed as an inflexible limitation on the scope of the exemplary embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments may be combined in any suitable manner in one or more embodiments. One skilled in the relevant art will recognize, in light of the description herein, that the exemplary embodiments can be practiced without one or more of the specific features or advantages of a particular embodiment. In other instances, additional features and advantages may be recognized in certain embodiments that may not be present in all embodiments of the subject disclosure.

FIGS. 1-12 illustrate an exemplary embodiment of an apparatus for evaluating motions of a joint. Specifically, the apparatus is a mechanical linkage system for measuring knee stability, but can alternatively be applied to any other joint of the body. In accordance with an aspect of the exemplary embodiment, the apparatus 10 includes a support frame 12, a fixation assembly 14 for securing a first body segment of a joint, and a displacement assembly 18 mounted to the support frame 12. The fixation assembly includes an axis of rotation moveable relative to the support frame. While FIGS. 1-12 illustrate the apparatus as applied to a right knee joint, the apparatus can equally be used for evaluating a left knee joint, such as by a mirrored construction of the apparatus or rotation of the apparatus to accommodate the left knee joint.

The anatomical joint described in connection with the exemplary embodiment is a knee joint. The knee joint includes, among other components, a tibia and a femur, with the femur articulating relative to the tibia or vice versa. Generally, the tibia moves relative to the femur in six degrees of freedom, three translations (medial/lateral, anterior/posterior, proximal/distal) and three rotations (flexion/extension, varus/valgus, internal/external). The tibia flexes relative to the femur throughout a full range of motion from hyperextension to excess of about 145° flexion. The tibia also internally and externally rotates relative to the femur as the tibia flexes throughout a range of motion. Moreover the knee joint has a certain degree of laxity such that the tibia can translate in the medial/lateral, anterior/posterior, and proximal/distal directions and rotate relative to the femur in the flexion/extension, varus/valgus, and internal/external directions.

In the exemplary embodiment, the femur of the patient is generally stationary, while the tibia is fixed to the apparatus 10. However, it is to be understood by those skilled in the art that the subject disclosure is not limited to any particular anatomical joint and can be applied to any anatomical joint or any mechanical joint i.e., two objects joined or united, either rigidly or in such a way as to permit motion. For instance, the exemplary embodiments of the subject disclosure are equally applicable to the ankle, wrist, elbow, hip, shoulder and any other joint of the human body. Moreover, the exemplary embodiments of the subject disclosure are not limited to body joints with any particular number of pivot axes. For example, the body joint could have one or two pivot axes without departing from the spirit and scope of the subject disclosure. Moreover, it is understood by those skilled in the art that the exemplary embodiments of the subject disclosure are equally applicable to non-human body joints, such as the knee joint of a monkey or ape, a prosthetic joint or a mechanical joint.

Referring now to FIGS. 1-3, 5 and 6, the apparatus 10 includes the support frame 12 upon which the displacement assembly 18 is mounted. As further discussed below, the displacement assembly includes a first frame 22 and second frame 24 each pivotably mounted to the support frame 12. The support frame 12 is preferably configured as a substantially square frame, as shown. However, the support frame 12 can be configured as any shape suitable for the foregoing intended use, e.g., rectangular, triangular, trapezoidal and the like. In accordance with an aspect of the exemplary embodiment, the support frame 12 can be rigidly attached to a subject (e.g., a patient) or a subject support structure such as a chair or a table and mounted in a fixed position relative to the displacement assembly 18.

Figure 5:
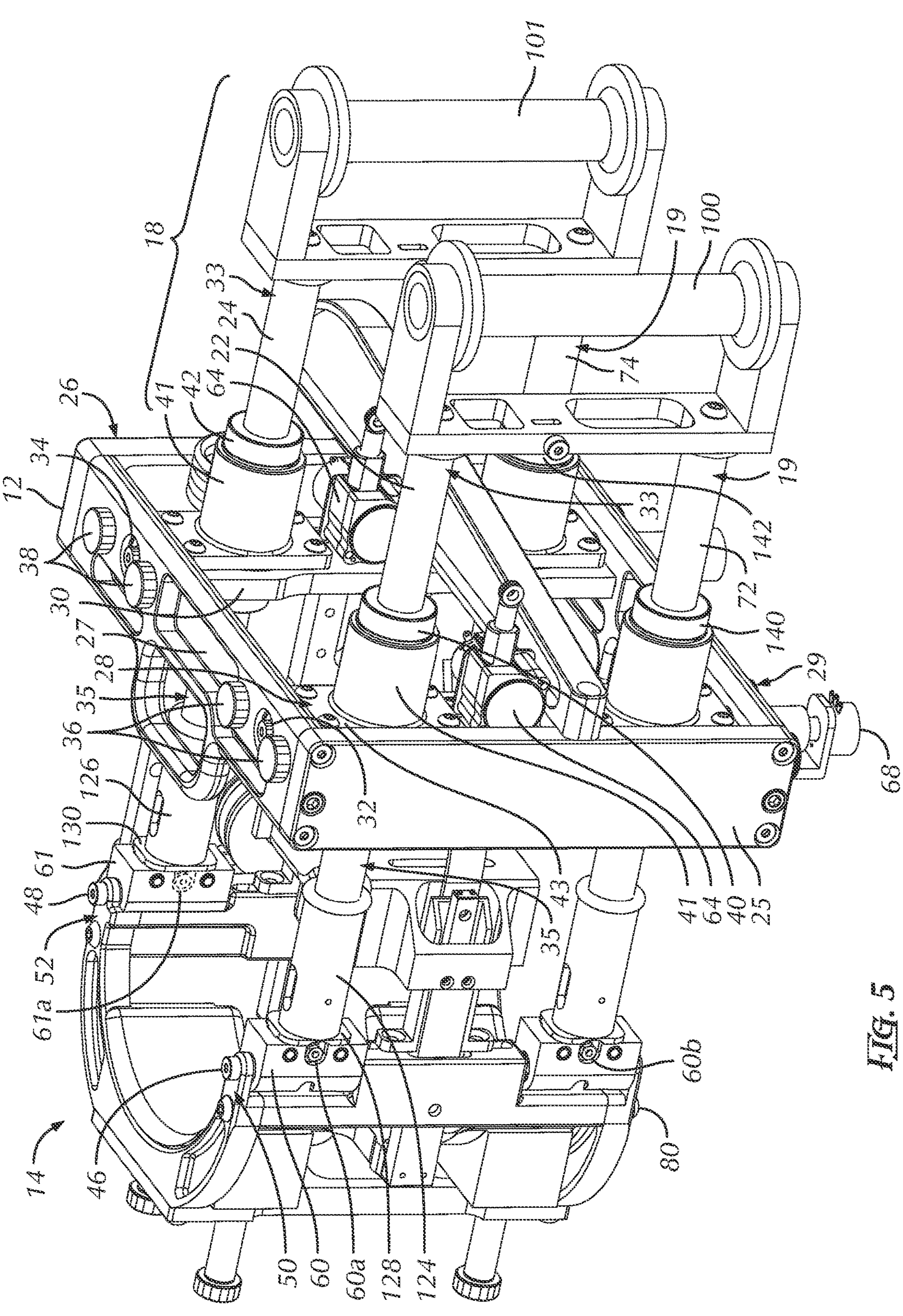
FIG. 5 is an enlarged perspective view of a fixation assembly and displacement assembly of the apparatus of FIG. 1.
Figure 6:
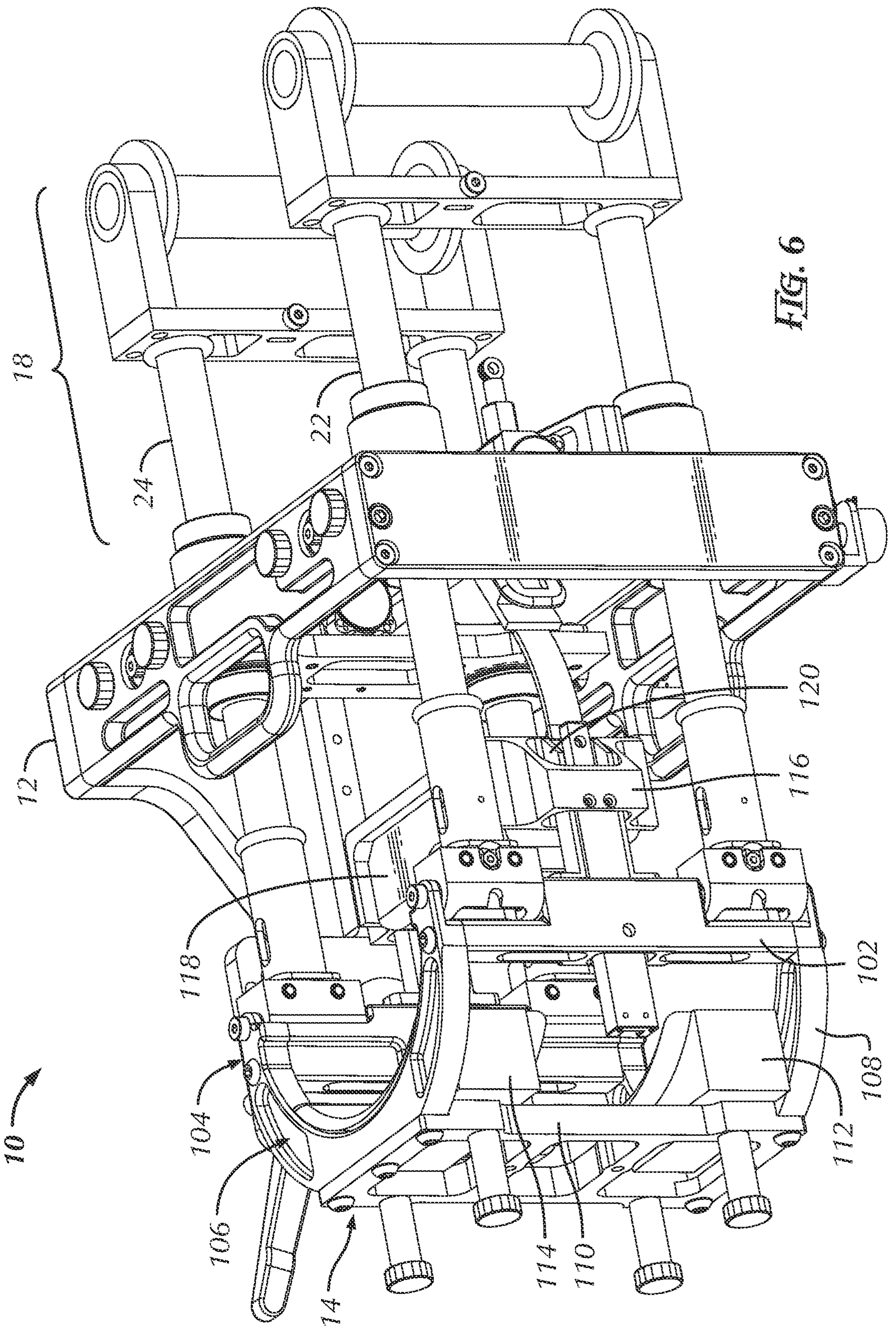
FIG. 6 is another enlarged perspective view of the fixation assembly and displacement assembly of FIG. 5.
Figure 7:
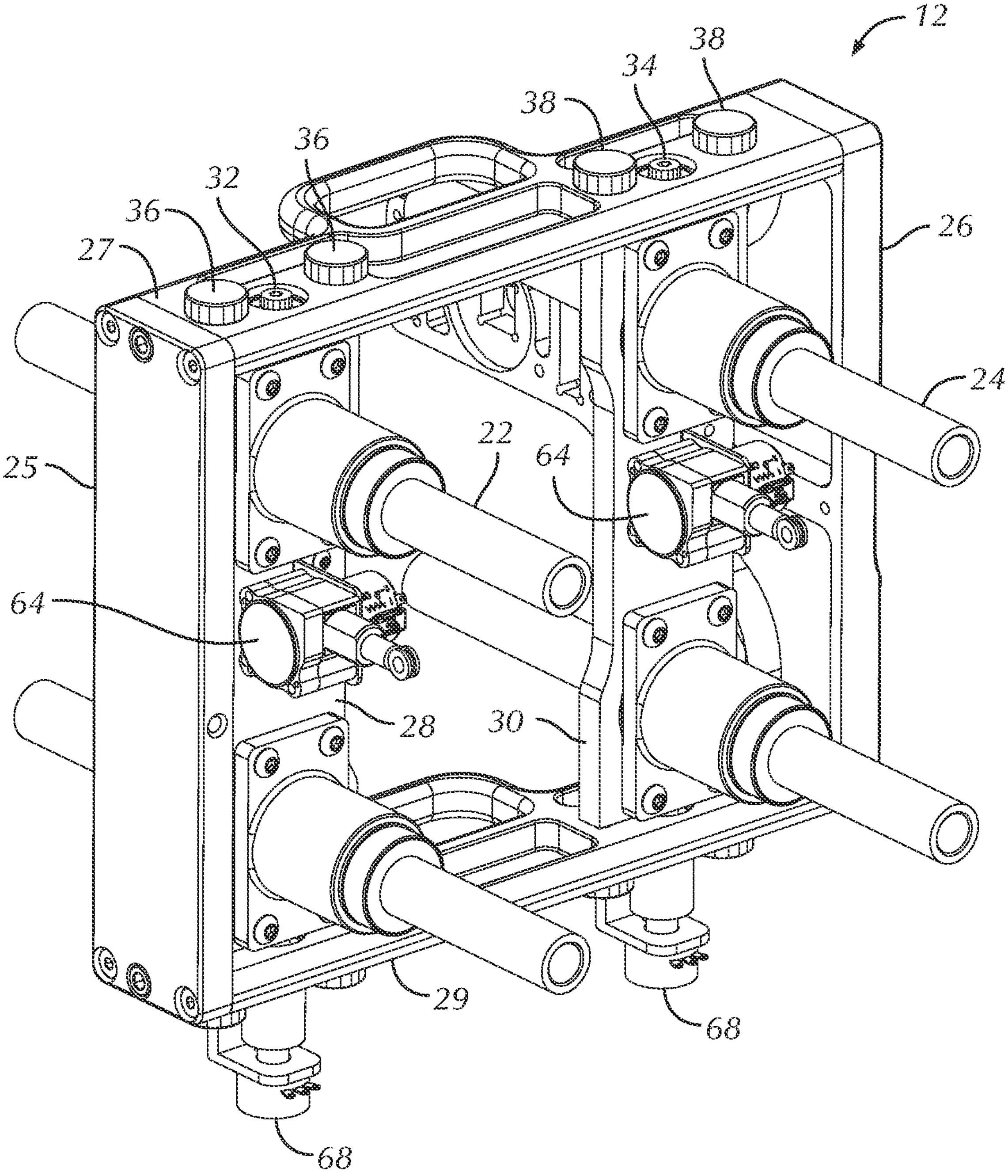
FIG. 7 is a perspective view of a support frame of the apparatus of FIG. 1.

In an exemplary embodiment shown in FIGS. 5-7, the support frame 12 includes an upper wall 27, a bottom wall 29 and a pair of side walls 25, 26. The upper wall 27, bottom wall 29 and side walls 25, 26 are configured to be substantially rectangular, as shown. However, the upper wall 27, bottom wall 29 and side walls 25, 26 can be configured as any shape suitable for their intended use, including but not limited to attaching the support frame 12 to a patient support structure such as a chair or attaching the support frame 12 to another apparatus or support frame.

The side walls 25, 26 are spaced apart to accommodate the first and second frames 22, 24 therebetween and extend generally parallel to each other. The upper wall 27 is attached to a dorsal end of the side walls 25, 26. The bottom wall 29 is attached to a ventral end of the side walls 25, 26. In accordance with an exemplary embodiment, the side walls 25, 26 are configured to be connectable to the upper wall 27 and bottom wall 29 e.g., via fasteners.

In accordance with an exemplary embodiment, the support frame 12 further includes a first shutter 28 and a second shutter 30 spaced from the first shutter 28. The first and second shutters 28, 30 are configured as shown in FIGS. 1, 5, 7 and 8. The first shutter 28 is rotatably connected to the upper wall and bottom wall about a first end of the support frame 12. The second shutter 30 is rotatably connected to the upper wall and bottom wall about a second end of the support frame 12 opposite the first end. For purposes of illustration, the first shutter 28 will be primarily described below. It is to be understood, however, that the first shutter 28 is similarly configured to the second shutter 30.

Each shutter 28, 30 has a first end rotatably connected to the upper wall 27 of the support frame and a second end opposite the first end rotatably connected to the bottom wall 29. Specifically, each shutter 28, 30 is rotatably secured to the respective upper and bottom walls by e.g., fasteners, such as bolts or pins. The fasteners 32, 34 can include a bearing surface or be configured as bearings themselves. The fasteners 32, 34 allow for rotation about a central rotational axis, such that each shutter 28, 30 can be freely rotated about the respective fastener 32, 34 during use. As such, each shutter 28, 30 is configured to pivot about a rotational axis substantially parallel to a longitudinal length of the shutter.

Figure 8:
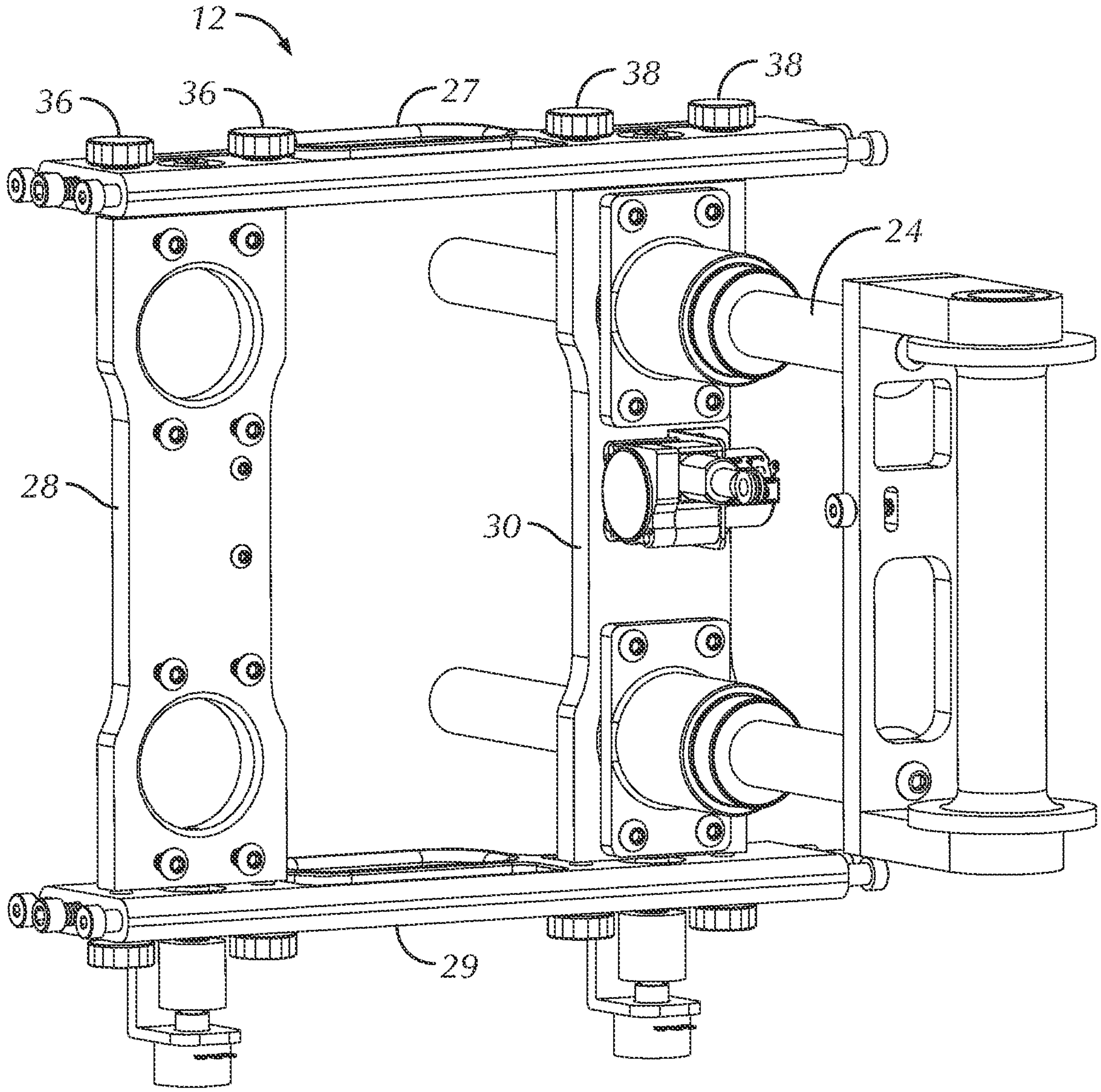
FIG. 8 is a perspective view of a pair of shutters of the apparatus of FIG. 1.

As shown in FIGS. 5, 7 and 8, each shutter 28, 30 is generally configured to be substantially rectangular. However, the shutters can alternatively be configured as any other shape suitable for their intended purpose e.g., cubical, cylindrical, parallelogram and the like. As further discussed below, each shutter 28, 30 includes a pair of spaced apart apertures for receiving the first frame 22 and second frame 24 of the displacement assembly 18 therethrough. In other words, the first frame 22 and second frame 24 are respectively pivotably mounted to the support frame 12 via the shutters 28, 30. In an aspect, the first and second frames 22, 24 can rotate and translate relative to the support frame 12. Additionally, each of the first and second frames 22, 24 includes a free end, i.e. distal end 33, moveable relative to the support frame 12.

Figure 9:
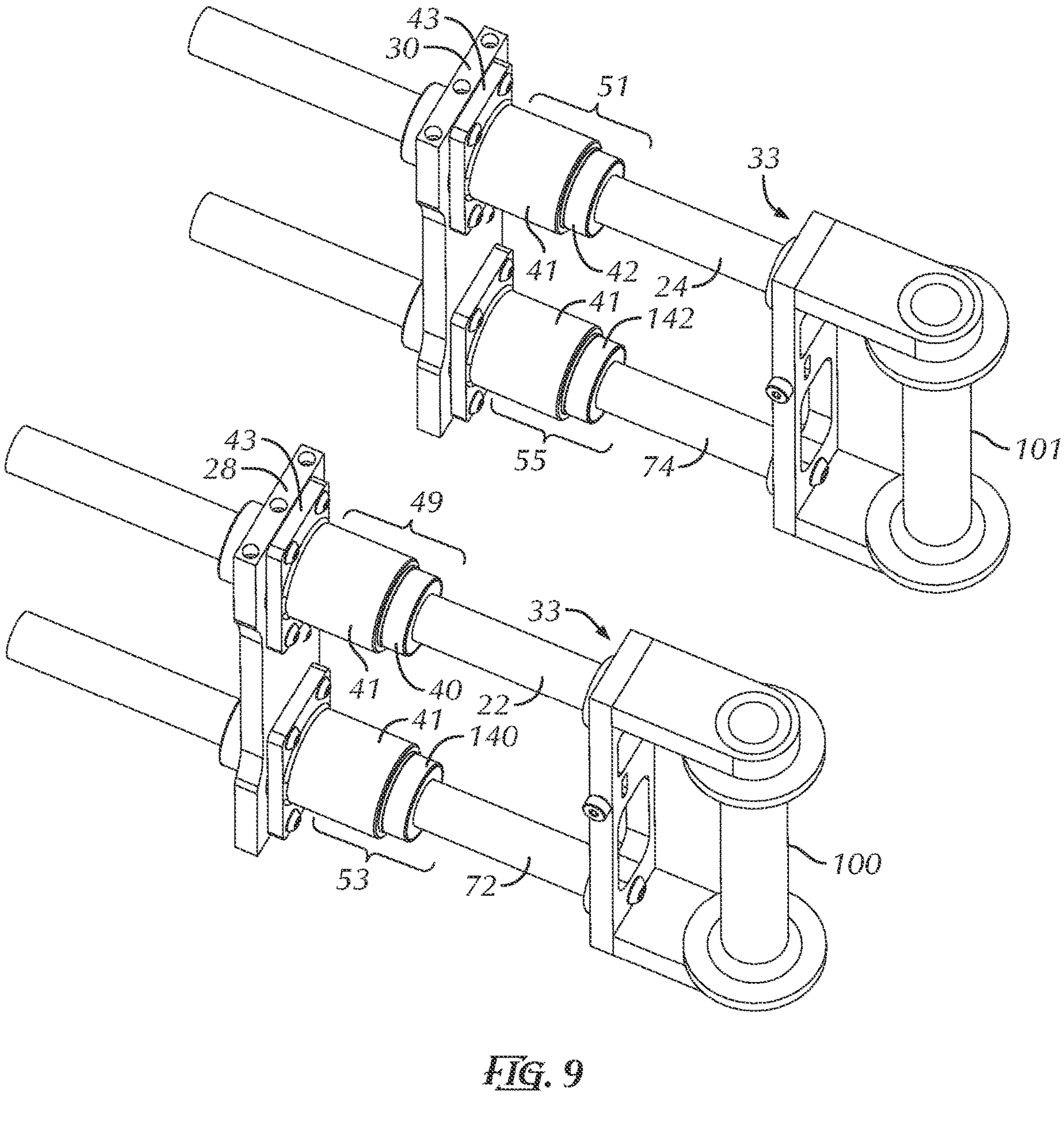
FIG. 9 is a perspective view of various components of a displacement assembly of the apparatus of FIG. 1.

In accordance with an exemplary embodiment of the subject disclosure shown in FIGS. 5, 6 and 9, the displacement assembly 18 includes first frame 22 pivotably mounted to the support frame 12 and rotatably connected to a first end of the fixation assembly 14 and second frame 24 pivotably mounted to the support frame 12 and rotatably connected to a second end of the fixation assembly 14. For purposes of illustration, first frame 22 will be primarily described below. It is to be understood, however, that first frame 22 is similarly configured to the second frame 24.

As shown in FIGS. 5 and 9, each of the first and second frames 22, 24 is preferably configured as an elongated shaft. The first and second frames 22, 24 include distal end 33 about a first end of the first and second frames 22, 24 for securing to a pair of handles (as further discussed below) and a proximal end 35 about a second end of the first and second frames 22, 24 opposite the first end and rotatably connected to the fixation assembly 14.

Each of the first and second frames 22, 24 is generally a cylindrical member having a longitudinal central axis and a circular longitudinal cross-section. However, the first and second frames 22, 24 can have any shaped cross-section such as hexagonal, polygonal or any other shape suitable for their intended purpose. The first and second frames 22, 24 can also be formed with a plurality of frame segments having different cross-sectional diameters. However, the first and second frames 22, 24 preferably have a uniform cross-sectional diameter.

For purposes of clarity, the present exemplary embodiment refers to both the first frame 22 and the second frame 24 in the figures, but only the structure of the first frame 22 in relation to the support frame 12 will be generally described below and it is to be understood that the second frame 24 can be e.g., a mirror image, or similar, or the same construction as the first frame 22. Additionally, the second frame 24 is similarly connected to the support frame 12 as the first frame 22 is connected to the support frame.

As best shown in FIGS. 5 and 9, the first frame 22 is supported by and extends through apertures on the first shutter 28 of the support frame 12. Specifically, the first frame 22 is supported by and extends through a housing 41 connected to the first shutter 28. The housing 41 is configured to house a linear bearing 40 and is rigidly mounted to the first shutter 28. Collectively, the linear bearing 40 and housing 41 form a first slide link 49. The first slide link 49 is slidably connected to the first frame 22. As shown in FIGS. 5 and 9, the bearing is configured as a linear bearing, but alternatively can be any type of bearing suitable for its intended purpose e.g., an annular bearing, a spherical bearing and the like.

In accordance with an aspect, the housing 41 is rigidly mounted to the first shutter 28 via a mounting bracket 43. The mounting bracket 43 is configured as a rectangular plate with a plurality of slots for receiving suitable fasteners, e.g., screws, pins, bolts, for affixing the housing 41 to the first shutter 28.

The housing 41 extends parallel to a longitudinal axis of the first frame 22. As used herein, the term “parallel” includes substantially parallel, while the term “substantially parallel” includes the ordinary meaning of parallel. The first shutter 28 is fixedly attached to the housing 41 so as to not rotate about the housing 41. The linear bearing 40 slidingly engages the housing 41, collectively forming the first slide link 49.

In other words, the first frame 22 is slidably connected to the support frame 12 via the first slide link 49, and the second frame 24 is slidably connected to the support frame 12 via a second slide link 51. Similar to the first slide link 49, the second slide link 51 includes a housing 41 configured to house a linear bearing 42. The linear bearings 40, 42 are slidably connected to respective housings 41 and allow for translation along a longitudinal axis of the first and second frames 22, 24, respectively. The housings 41 are rigidly mounted to respective first and second shutters 28, 30. Alternatively expressed, the first frame 22 is slidably connected to the support frame 12 via the first slide link 49, and the second frame 24 is slidably connected to the support frame 12 via the second slide link 51. Specifically, the first slide link 49 is pivotably connected to the support frame 12 via the first shutter 28. Similarly, the second slide link 51 is pivotably connected to the support frame 12 via the second shutter 30.

Referring now to FIGS. 5 and 9, the support frame 12 rotatably supports the first and second shutters 28, 30 and the first and second slide links 49, 51 for rigidly fixating the first and second slide links 49, 51 on the support frame 12.

The support frame also includes a first locking mechanism 36 and a second locking mechanism 38 for maintaining a rotational position of the respective shutters 28, 30. The first and second locking mechanism 36, 38 can be any suitable fasteners, e.g., screws, pins, bolts, for adjustably securing a position of the respective shutters 28, 30.

In accordance with an exemplary embodiment, the fixation assembly 14 is configured as shown in FIGS. 1, 6, 10 and 11. As discussed above, the proximal end of the first and second frames 22, 24 is rotatably connected to the fixation assembly 14. Specifically, the first frame 22 is rotatably connected to a first end 50 of the fixation assembly 14 and the second frame 24 is rotatably connected to a second end 52 of the fixation assembly 14. As best shown in FIG. 5, the first end 50 of the fixation assembly 14 is spaced from and opposite the second end 52 of the fixation assembly 14. In general, the fixation assembly 14 is configured to receive a first body segment of the joint.

Figure 10:
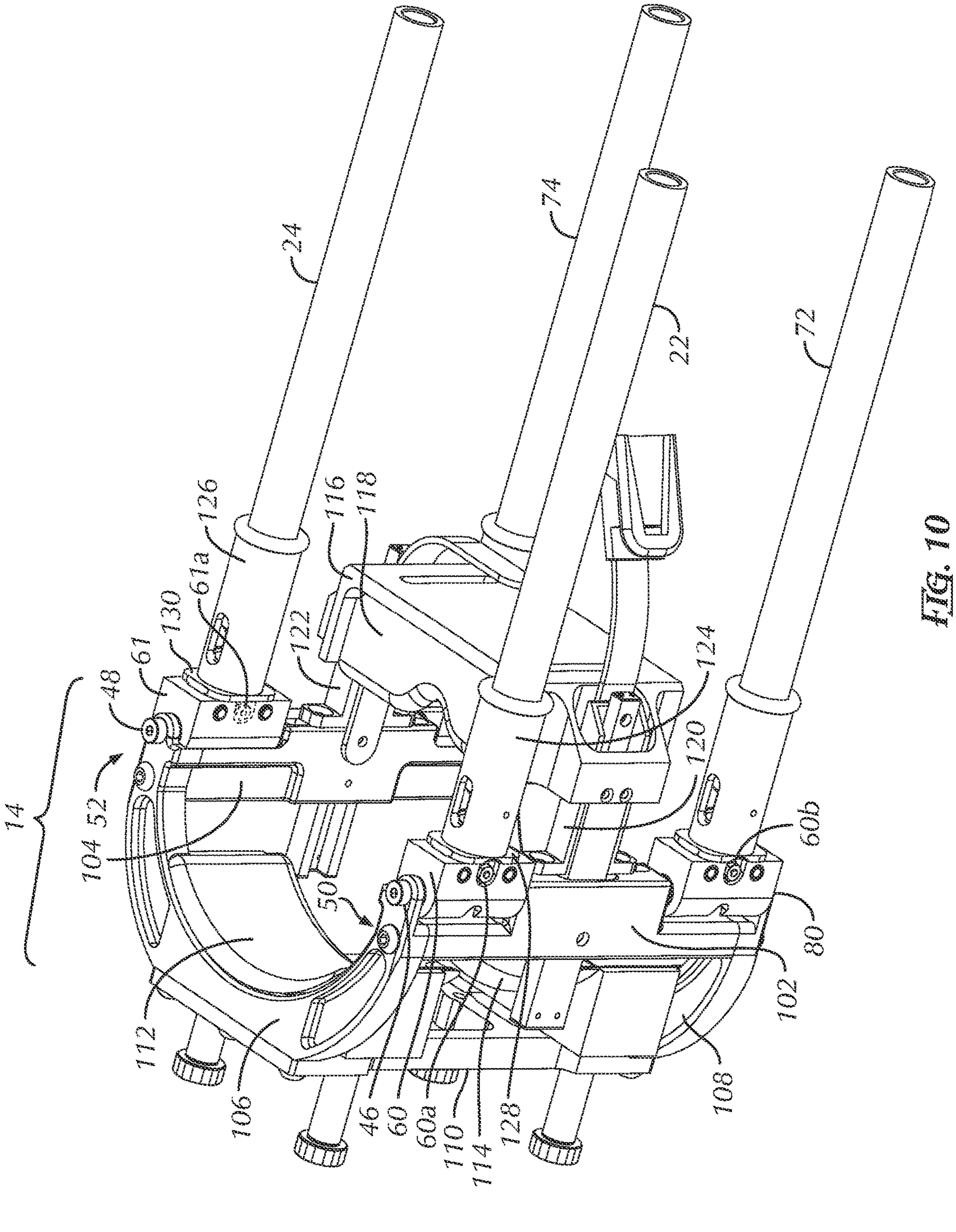
FIG. 10 is a perspective view of a fixation assembly of the apparatus of FIG. 1.

Referring now to FIG. 10, the first frame 22 and second frame 24 are rotatably connected to the fixation assembly 14. The fixation assembly 14 includes first and second sidewalls 102, 104 which are spaced apart to accommodate the first body segment therebetween and extend generally parallel to each other. An upper wall 106 is pivotably attached to a dorsal end of the first and second sidewalls 102, 104 by a fastener. Similarly, a bottom wall 108 is pivotably attached to a ventral end of the first and second sidewalls 102, 104. The fixation assembly 14 further includes a backing plate 110 fixedly attached to respective posterior ends of the upper wall 106 and bottom wall 108 for providing structural support to the fixation assembly 14.

The fixation assembly 14 includes a first and a second pad 112, 114 extending inwardly from the backing plate 110 and adjustably positioned along a longitudinal axis of the backing plate 110. As shown in FIG. 10, the first pad 112 is positioned adjacent a dorsal end of the first and second sidewalls 102, 104 and the second pad 114 is positioned adjacent a ventral end of the first and second sidewalls 102, 104 for securing a first body segment of the joint.

The upper wall 106, bottom wall 108, first pad 112 and second pad 114 are configured as substantially semi-circular members for receiving a leg of a patient. However, the upper wall 106, bottom wall 108, first pad 112 and second pad 114 can be configured as any shape suitable for their intended use. In accordance with an exemplary embodiment, the first and second sidewalls 102, 104 are configured to be connectable to the upper wall 106 and bottom wall 108 via fasteners e.g., screws, pins, and bolts for affixing the respective walls.

Figure 11:
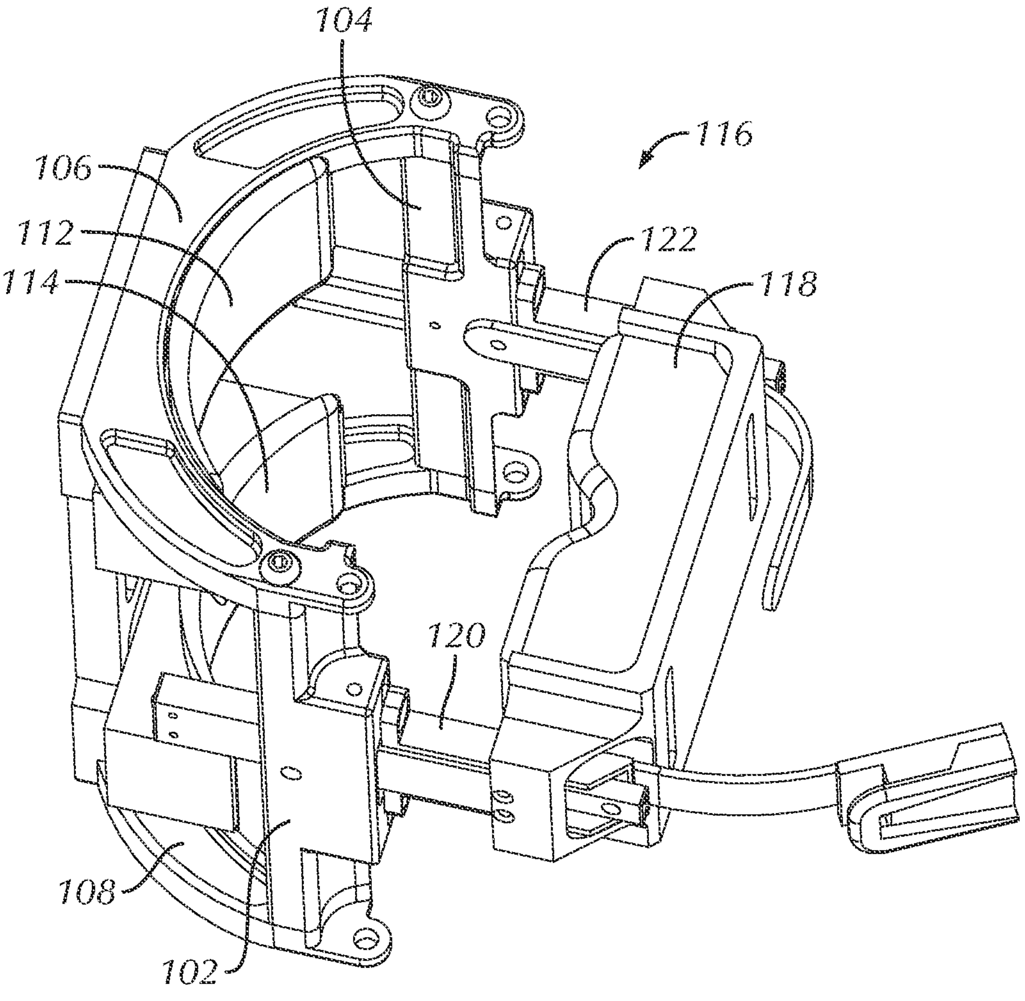
FIG. 11 is a perspective view of an adjustable clamp of the apparatus of FIG. 1.
Figure 12:
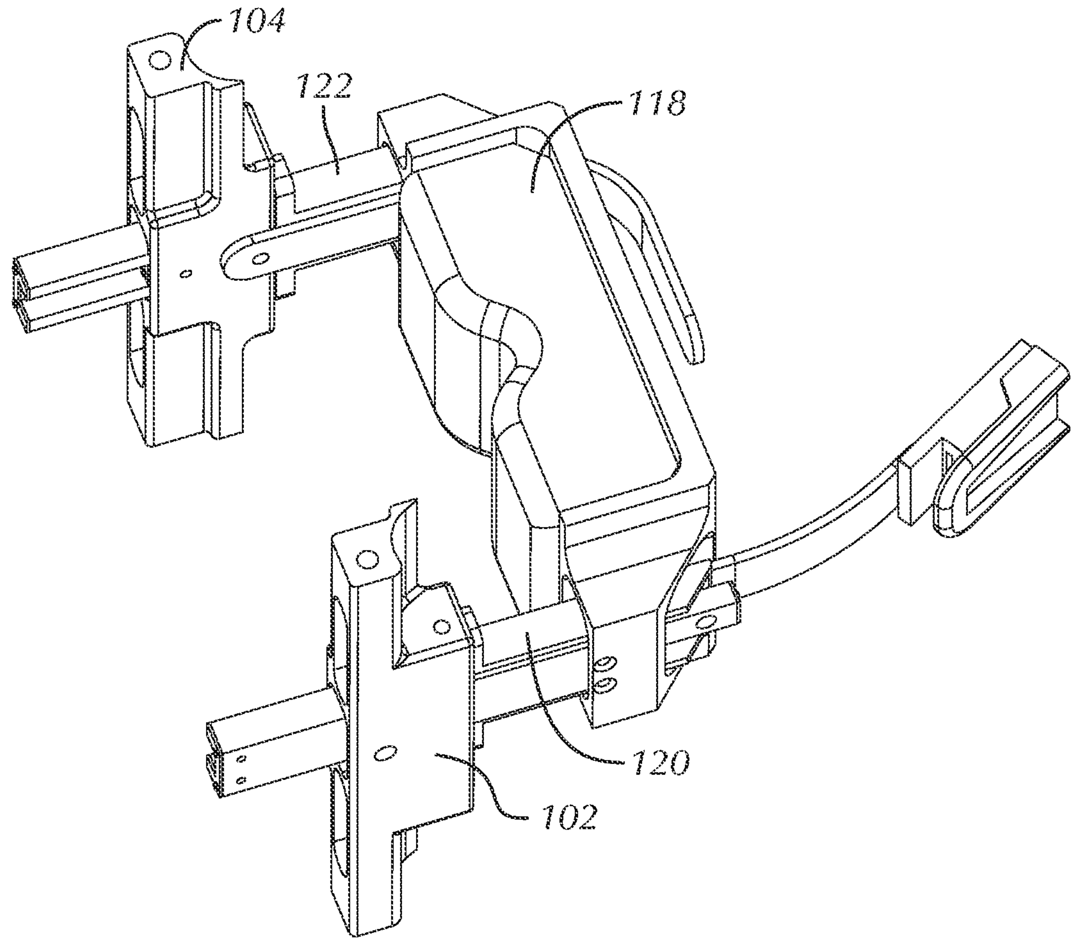
FIG. 12 is a perspective view of various components of the adjustable clamp of FIG. 11.

As best shown in FIGS. 10-12, the fixation assembly 14 further includes an adjustable clamp 116 slidably connected to the first and second sidewalls 102, 104. Specifically, the adjustable clamp 116 is slidably connected to a pair of guide rails 120, 122 respectively extending from the first and second sidewalls 102, 104. The adjustable clamp 116 further includes a fixation wedge 118 for securing a first body segment of the joint. The fixation wedge 118 is configured as a substantially semi-circular cutout for receiving a leg of a patient. In operation, the adjustable clamp 116 can be positioned at a plurality of positions along the guide rails 120, 122 to adjustably secure the apparatus 10 to patients with various knee dimensions.

Referring back to FIGS. 5 and 10, the first and second frames 22, 24 are rotationally connected to the fixation assembly 14 by a pair of respective rotational joints 46, 48. The first frame 22 is rotatably connected to rotational joint 46 about the first end 50 of the fixation assembly 14. Similarly, the second frame 24 is rotatably connected to rotational joint 48 about the second end 52 of the fixation assembly 14.

As best shown in FIG. 10, the first frame 22 is supported by and extends through a guide tube 124. The guide tube 124 is rigidly mounted to a bearing block 60 via a mounting bracket 128. The bearing block 60 is pivotably coupled to the upper wall 106 by the first rotational joint 46. Similarly, the second frame 24 is supported by and extends through a guide tube 126. The guide tube 126 is rigidly mounted to a bearing block 61 via a mounting bracket 130. The bearing block 61 is pivotably coupled to the upper wall 106 by the second rotational joint 48. The mounting brackets 128, 130 are configured as a plate with a plurality of slots for receiving suitable fasteners, e.g., screws, pins, bolts, for affixing the guide tubes 124, 126 to the respective bearing blocks 60, 61. As further discussed below, the bearing blocks 60, 61 include a pair of respective force sensors **60*a*, 61*a*** for measuring side to side forces (i.e., medial/lateral forces) or up and down forces (i.e., compression/distraction forces).

The guide tubes 124, 126 extend parallel to a longitudinal axis of the first and second frames 22, 24. The guide tubes 124, 126 are configured as hollow elongated cylindrical shafts sized and shaped to allow the first and second frames 22, 24 to slidably pass therethrough. The guide tubes 124, 126 have a larger cross-sectional diameter than a cross-sectional diameter of the respective first and second frames 22, 24. In sum, the first and second frames 22, 24 are rotationally connected to the fixation assembly 14 via bearing blocks 60, 61, wherein the bearing blocks 60, 61 are pivotably coupled to the fixation assembly 14.

In accordance with an aspect of the exemplary embodiment, the guide tubes 124, 126 are each configured as a bushing and include a respective force sensor (not shown), e.g., a load cell, attached in series with the first and second frames 22, 24 for measuring applied load forces on the fixation assembly 14. The guide tubes 124, 126 provide support and protection to the respective load cells positioned within the guide tubes 124, 126. Specifically, the guide tubes 124, 126 mitigate or reduce any bending forces on the load cells from the first and second frames 22, 24.

Additionally, the fixation assembly 14 has an axis of rotation moveable relative to the support frame 12. In other words, the fixation assembly 14 has a floating axis of rotation relative to the support frame 12. The first and second frames 22, 24 are rotationally connected to the fixation assembly 14 by the respective rotational joints 46, 48 positioned about the first and second ends 50, 52. As previously discussed, the support frame 12 includes first and second locking mechanisms 36, 38 for securing the position of the respective shutters 28, 30. When a bone of the knee joint, e.g., the tibia is secured to the apparatus 10, the first and second frames 22, 24 are pivotably mounted to support frame 12 via the shutters 28, 30. The shutters 28, 30 can be secured in a desired position via the first and second locking mechanisms 36, 38 and the support frame 12 is fixed in position. However, the rotational joints 46, 48 and slide links 49, 51 allow the fixation assembly 14 to be moveable relative to the support frame thereby allowing an axis of the bone of the knee joint e.g., tibia, to be moveable relative to the fixed position of the support frame 12.

The shutters 28, 30 and slide links 49, 51 are preferably unlocked such that the first and second frames 22, 24 are allowed to translate and the shutters 28, 30 are allowed to rotate freely to allow measurement and determination of the axis of rotation of the tibia. If both shutters 28, 30 are secured in a desired position, only translational motion of the first and second frames 22, 24 can occur. If only one of the shutters 28, 30 is secured, the knee joint can be strained about a side with the secured shutter. In an alternative aspect, the first and second frames 22, 24 can be secured with a clamping mechanism, e.g., a collar.

In accordance with another aspect of the exemplary embodiment shown in FIGS. 5, 9 and 10, the displacement assembly 18 can optionally include a third frame 72 pivotably mounted to the support frame 12 and rotatably connected to the first end 50 of the fixation assembly 14. Specifically, the third frame 72 is rotatably connected to the first end 50 of the fixation assembly 14 via rotational joint 80. Additionally, the displacement assembly 18 can further optionally include a fourth frame 74 pivotably mounted to the support frame 12 and rotatably connected to the second end 52 of the fixation assembly 14. Specifically, the fourth frame 74 is rotatably connected to the second end 52 of the fixation assembly 14 via rotational joint 82. For purposes of convenience, only rotational joint 80 of the respective rotational joints 80, 82 is illustrated. It is to be understood, however, that rotational joint 82 is a mirror image construction of rotational joint 80. Additionally, the third frame 72 and fourth frame 74 are similarly configured to the first and second frames 22, 24, respectively as described above. As such, each of the third and fourth frames 72, 74 includes a free end moveable relative to the support frame 12.

In accordance with an exemplary embodiment, the first and second frames 22, 24 form a first linkage plane. Specifically, the first and second frames 22, 24, upper wall 106 of the fixation assembly 14, and the support frame 12 collectively form the first linkage plane. As shown in FIG. 5, the first and second frames 22, 24 are pivotably mounted to the support frame 12 via the first and second slide links 49, 51 and the first and second shutters 28, 30 previously described. Additionally, the first and second frames 22, 24 are rotationally connected to the upper wall 106 of the fixation assembly 14 by respective rotational joints 46, 48. The first frame 22 is rotatably connected to rotational joint 46 and the second frame 24 is rotatably connected to rotational joint 48. Collectively, the foregoing components form the first linkage about a single plane.

In accordance with an exemplary embodiment, the third and fourth frames 72, 74 form a second linkage plane. Specifically, the third and fourth frames 72, 74, bottom wall 108 of the fixation assembly 14, and the support frame 12 collectively form the second linkage plane. As shown in FIG. 5, the third and fourth frames 72, 74 are pivotably mounted to the support frame 12 via a pair of slide links 53, 55 and the first and second shutters 28, 30 previously described. Similar to the first and second slide links 49, 51, the third and fourth slide links 53, 55 include respective housings 41 configured to house linear bearings 140, 142. The linear bearings 140, 142 are slidably connected to respective housings 41 and allow for translation along a longitudinal axis of the third and fourth frames 72, 74, respectively. Additionally, the third and fourth frames 72, 74 are rotationally connected to the bottom wall 108 of the fixation assembly 14 by respective rotational joints 80, 82. The third frame 72 is rotatably connected to rotational joint 80 and the fourth frame 74 is rotatably connected to rotational joint 82. Collectively, the foregoing components form the second linkage about a single plane.

It is to be understood that the first linkage plane formed by the first and second frames 22, 24 is similarly configured to the second linkage plane formed by the third and fourth frames 72, 74. As configured and shown in FIG. 5, the first linkage plane is parallel to the second linkage plane. Alternatively expressed, the first and second frames 22, 24 form a first displacement assembly and third and fourth frames 72, 74 form a second displacement assembly 19 similar to the first displacement assembly. Additionally, the rotational joints 46, 80 of the respective first and third frames 22, 72 are aligned such that they form a single rotational axis about the first end 50 of the fixation assembly 14. Similarly, the rotational joints 48, 82 of the respective second and fourth frames 24, 74 are aligned such that they form a single rotational axis about the second end 52 of the fixation assembly 14.

Referring now to FIGS. 5 and 9, the displacement assembly 18 further includes a first handle 100 attached to the distal end of the first and third frames 22, 72 and a second handle 101 attached to the distal end of the second and fourth frames 24, 74, each for applying a load to the fixation assembly 14. In accordance with another exemplary embodiment, the first handle 100 is only attached to a distal end of the first frame 22 and the second handle 101 is only attached to a distal end of the second frame 24.

As shown in FIG. 9, each of the first and second handles 100, 101 is preferably configured as an elongated shaft. For purposes of convenience, only the first handle 100 will be described below. However, it is to be understood that first handle 100 is similarly configured to the second handle 101.

The first handle 100 is generally a cylindrical member having a longitudinal central axis and a circular longitudinal cross-section. However, the first handle 100 can have any shaped cross-section such as hexagonal, polygonal or any other shape suitable for its intended purpose. The first handle 100 can also be formed with a plurality of handle segments having different cross-sectional diameters. However, the first handle 100 preferably has a uniform cross-sectional diameter.

The first handle 100 may include gripping portions that aid a user's ability to grip and move the first handle 100. The gripping portion is preferably disposed throughout the length of the handle to aid in gripping the first handle. The gripping portion may be shaped as any suitable shape that may aid a user's ability to grip the first handle such as knurlings, finger slots, depressions, grooves or a textured surface.

Referring now to FIG. 5, the first and second handles 100, 101 can be used to apply a load to the fixation assembly 14. Specifically, a user can use the handles 100, 101 to apply a force to move the first, second, third and fourth frames 22, 24, 72, 74 in a linear direction along the respective linear bearings 40, 42, 140, 142. In other words, a load force applied to the first and second handles 100, 101 generates a load force on the fixation assembly 14 through the bearing blocks 60, 61, and thereby a load force to the joint bone within the fixation assembly. When the apparatus is secured to a user, the support frame 12 is fixed in position. As further discussed below, a plurality of sensors can be used to measure rotational and translational motion relative to the support frame 12.

In accordance with an exemplary embodiment, the bearing blocks 60, 61 each include a force sensor 60*a*, 61*a*. Each force sensor 60*a*, 61*a* is attached in series with the respective first and second frame 22, 24 to measure the applied load force on the fixation assembly 14. It is to be understood that the third and fourth frames 72, 74 each include a respective force sensor 60*b*, 61*b* to measure the applied load force from the frame on the fixation assembly 14. The force sensors 60*a*, 61*a*, 60*b*, 61*b* inside bearing blocks of respective frames 22, 24, 72, 74 measure medial/lateral forces and varus/valgus torques. For purposes of convenience, only force sensors 60*a*, 60*b*, 61*a* of the respective force sensors 60*a*, 61*a*, 60*b*, 61*b* are illustrated. It is to be understood, however, that force sensor 61*b* is the same or similar to force sensor 60*b*.

As previously discussed, the guide tubes 124, 126 each include a respective force sensor, e.g., a load cell, attached in series with the first and second frames 22, 24. It is to be understood that the third and fourth frames 72, 74 also each include a respective force sensor, e.g., a load cell, attached in series with the third and fourth frames 72, 74. The force sensors in the guide tubes 124, 126 measure applied load forces along a long axis of the respective frames 22, 24, 72, 74.

In sum, a plurality of force sensors are operatively connected to the displacement assembly 18 for measuring a force applied to the fixation assembly 14. Collectively, the plurality of force sensors can be used to measure internal/external rotational torque forces, anterior/posterior forces, varus/valgus rotational torque forces, and compression/distraction forces. In an aspect of the exemplary embodiment, additional sensors can be used to measure compression forces along multiple axes of the apparatus 10.

In accordance with an exemplary embodiment, the apparatus 10 further comprises a translational sensor 64 operatively connected to the displacement assembly 18 for measuring a translation of at least one of the first and second frames 22, 24. Specifically, the translational sensor 64 measures displacement of at least the one of the first and second frames 22, 24 upon application of a force, such as a force supplied by a user through the first and second handles 100, 101.

In accordance with an exemplary embodiment, the apparatus 10 further includes a rotational sensor 68, e.g., a potentiometer, operatively connected to the displacement assembly 18 for measuring a rotational position of at least one of the first and second frames 22, 24. Specifically, the rotational sensor 68 measures the angular displacement of the joint upon application of a force supplied by a user through the first and second handles 100, 101. More specifically, the rotational sensor 68 measures angular displacement of the first and second frames 22, 24 relative to the support frame upon application of the force supplied by the user, so as to measure e.g., rotational movement of the knee joint. It is to be understood that the rotational sensor can be configured as any type of sensor suitable for its intended purpose, e.g., a dial potentiometer, an inductive rotary sensor, a Hall effect sensor and the like.

Applicable microprocessors, sensors, and potentiometers applicable to the exemplary embodiments are also disclosed in U.S. Pat. No. 5,335,674, the entire disclosure of which is incorporated by reference herein for all purposes.

In operation, measurement of the displacement of the joint and measurement of the force applied to a joint of a knee patient allows a user to determine the angle of rotation and the location of the axis of rotation of the knee joint. For example, in an exemplary use of the apparatus, the femur of a joint is fixed in position and the tibia is secured to the fixation assembly. As a result, the apparatus allows a user to measure the anterior-posterior, medial-lateral and rotational position of the joint, such as movement of the tibia relative to the femur, and such movement of the tibia relative to the femur as the joint moves through a range of motion. Specifically, the rotational joints 46, 48 identify the position of reference points on either side of the tibia allowing measurement of anterior/posterior translations of the medial and lateral compartments of a knee joint, the internal/external rotation of the knee joint, the angle of rotation of the knee joint, the location of the axis of rotation of the knee joint as the joint moves through a range of motions, and the location of the axis of rotation of the knee joint in a transverse plane corresponding to the first and second linkage plane of the apparatus. Measurement of the load-displacement response of the medial and lateral compartments of the knee by the force and positional sensors along with the measurement of displacement of the first and second frames relative to the support frame allows a user to calculate the angle of rotation and the location of the axis of rotation of the knee joint, e.g., the tibia relative to the support frame.

An operator, such as, a physician or surgeon can push and pull the first and second handles 100, 101 in a direction parallel to each of the frames. The forces can be applied independently or simultaneously to each frame. Also, the forces can be applied to only one of the first and second handles. Additionally, forces applied in an opposite direction causes a force couple, which generates torque directed inside the first and second linkage plane of the apparatus. For example, the force couple can generate internal and external rotation of the tibia with respect to the femur. The force sensors in series with the first and second frame can provide measurements of the applied forces.

Although the exemplary embodiments of the subject disclosure are discussed with respect to the transverse plane of a knee joint, the apparatus can be aligned in other anatomical planes to assess knee laxity. For example, it can be aligned with the frontal plane to allow measurements of abduction and adduction, medial and lateral laxities, and the axis of knee rotation in the frontal plane. It will be appreciated that multiple apparatuses may be combined to allow simultaneous measurements of laxity in more than one anatomical plane and identification of the axis of knee rotation in three dimensions. The exemplary embodiments of the subject disclosure are particularly advantageous because it accounts for internal/external rotations, compartmental translations, and adjusted positions of the axis of rotation of the tibia with respect to the femur in cases of injury, reconstruction, or replacement of the joint.

It will be appreciated by those skilled in the art that changes could be made to the exemplary embodiments described above without departing from the broad inventive concept thereof. For example, the rotational joints 46, 48, 80, 82 of the apparatus can be replaced with spherical joints to allow for 3D motions, i.e., multiplanar motions. As a result, an applied load force by an operator can include a rotational force in the flexion/extension, varus/valgus, and internal/external directions.

It is to be understood that the exemplary embodiment of the subject disclosure can also be integrated with other load displacement apparatuses disclosed e.g., in U.S. Pat. No. 9,566,022 and U.S. Patent App. Pub. No. 2017/0119284, the entire disclosures of which are incorporated by reference herein for all purposes.

In sum, the subject disclosure provides an apparatus and method for assessing laxity of a joint. For example, the subject disclosure enables application of forces on the medial and lateral sides of the knee joint to determine stability of the medial and lateral compartments of the knee. Such forces include pure torques via a force couple as well as simultaneous manual application of forces in multiple anatomical planes. Measurements from the sensors allow for identification of the axis of rotation of a joint. In other words, the apparatus is a linkage system that determines a position and orientation of a body in clinically relevant directions and the forces applied to the body.

The subject disclosure also provides a method of objectively assessing the joint laxity of an anatomical joint formed by a first body segment and a second body segment. The method includes providing an apparatus for evaluating motions of a joint as described above. The method also includes the steps of securing or positioning the first body segment (e.g., a femur or thigh), while fixing the second body segment (e.g., a tibia) to a fixation assembly, such as the fixation assembly 14 described in the above exemplary embodiment. The method further includes the step of applying a force to the joint and then measuring displacement of the tibia relative to the femur upon application of the force as well as measuring the forces applied to the tibia, i.e., the second body segment. The step of applying a force to the joint can be performed manually by an operator such as a physical therapist or a surgeon pushing and pulling on a displacement assembly, such as the displacement assembly 18 described in the above exemplary embodiment.

The method further includes the step of applying forces in opposing directions to generate torque forces resulting in, for example, internal and external rotation of the tibia with respect to the femur. The method includes the step of measuring rotational and translational motion of the displacement assembly relative to the support frame through a plurality of sensors. The displacement of the tibia relative to the femur upon application of the force is determined by measuring displacement of the first and second frames relative to the support frame. Application of forces on the medial and lateral sides of the joint with the exemplary embodiment of the subject disclosure allows for measuring stability of the knee joint e.g., medial and lateral compartments of a joint, as well as determining a position of an axis of rotation of one of the joint bones as the joint moves through a range of motion.

It will be appreciated by those skilled in the art that changes could be made to the exemplary embodiments described above without departing from the broad inventive concept thereof. It is to be understood, therefore, that the subject disclosure is not limited to the particular exemplary embodiments disclosed, but it is intended to cover modifications within the spirit and scope of the subject disclosure as defined by the appended claims.

I claim:

1. An apparatus for evaluating motions of a joint comprising:
- a fixation assembly for securing a first body segment of a joint; and
- a displacement assembly that includes:
  - a first actuator pivotably connected to a first end of the fixation assembly,
  - a second actuator pivotably connected to a second end of the fixation assembly,
  - a third actuator pivotably connected to the first end of the fixation assembly, and
  - a fourth actuator pivotably connected to the second end of the fixation assembly.

2. The apparatus of claim 1, further comprising a support frame supporting the displacement assembly.

3. The apparatus of claim 2, wherein the first actuator is pivotably mounted to the support frame.

4. The apparatus of claim 2, wherein the second actuator is pivotably mounted to the support frame.

5. The apparatus of claim 1, wherein the first end of the fixation assembly is spaced from and opposite the second end of the fixation assembly.

6. The apparatus of claim 1, wherein the fixation assembly has an axis of rotation and is rotatable about the axis of rotation.

7. The apparatus of claim 6, wherein movement of at least one of the first actuator and the second actuator moves the fixation assembly about the axis of rotation.

8. The apparatus of claim 6, wherein the axis of rotation is substantially transverse to a longitudinal direction of travel of the first actuator or second actuator.

9. The apparatus of claim 1, wherein a first end of the first actuator is movable relative to the support frame.

10. The apparatus of claim 1, wherein the first actuator is movable relative to the second actuator.

11. The apparatus of claim 1, further comprising a force sensor operatively connected to the displacement assembly for measuring a force applied to the fixation assembly.

12. The apparatus of claim 1, further comprising a translational sensor operatively connected to the displacement assembly for measuring a translation of one of the first and second actuators.

13. The apparatus of claim 1, further comprising a rotational sensor operatively connected to the displacement assembly for measuring a rotational position of one of the first and second actuators.

14. The apparatus of claim 1, wherein the displacement assembly further comprises a first handle attached to the first and third actuators and a second handle attached to the second and fourth actuators, each for applying a load to the fixation assembly.

15. The apparatus of claim 1, wherein the third actuator is pivotably mounted to the support frame.

16. The apparatus of claim 1, wherein the fourth actuator is pivotably mounted to the support frame.

17. The apparatus of claim 1, wherein the displacement assembly further comprises a first handle attached to the first actuator and a second handle attached to the second actuator, each for applying a load to the fixation assembly.

18. An apparatus for evaluating motions of a joint-comprising:
- a fixation assembly for securing a first body segment of a joint; and
- a displacement assembly that includes:
  - a first actuator configured to translate a first end of the of the fixation assembly and pivotably connected thereto, a second actuator configured to translate a second end of the of the fixation assembly and pivotably connected thereto, a third actuator configured to translate a first end of the of the fixation assembly and pivotably connected thereto, and a fourth actuator configured to translate a first end of the of the fixation assembly and pivotably connected thereto.

* * * * *